US00PP24906P3

(12) United States Plant Patent
van Lankveld

(10) Patent No.: US PP24,906 P3
(45) Date of Patent: Sep. 23, 2014

(54) *STROBILANTHUS* PLANT NAMED 'LANKVELD13'

(50) Latin Name: *Strobilanthes anisophyllus*
Varietal Denomination: Lankveld13

(71) Applicant: Martinus T. M. van Lankveld, Elsendorp (NL)

(72) Inventor: Martinus T. M. van Lankveld, Elsendorp (NL)

( * ) Notice: Subject to any disclaimer, the term of this patent is extended or adjusted under 35 U.S.C. 154(b) by 65 days.

(21) Appl. No.: 13/815,303

(22) Filed: Feb. 19, 2013

(65) Prior Publication Data

US 2013/0247257 P1 Sep. 19, 2013

(51) Int. Cl.
*A01H 5/00* (2006.01)

(52) U.S. Cl.
USPC ..... Plt./226

(58) Field of Classification Search
CPC ..... A01H 1/00; A01H 1/02; A01H 1/04; A01H 3/00; A01H 3/04; A01H 4/005; A01H 5/02
USPC ..... Plt./226
See application file for complete search history.

*Primary Examiner* — Annette Para
(74) *Attorney, Agent, or Firm* — Penny J. Aguirre

(57) ABSTRACT

A new cultivar of *Strobilanthes anisophyllus*, 'Lankveld13', that is characterized by its leaves that are dark purple-black to dark green-purple in color, its numerous flowers per stem, and its compact plant habit.

2 Drawing Sheets

Botanical classification: *Strobilanthes anisophyllus*.
Variety denomination: 'Lankveld13'.

BACKGROUND OF THE INVENTION

The present invention relates to a new and distinct cultivar of *Strobilanthes anisophyllus* and will be referred to hereafter by its cultivar name, 'Lankveld13'. 'Lankveld13' is a new evergreen shrub grown for use as an ornamental landscape plant.

The Inventor discovered the new cultivar in June of 2008 as a naturally occurring branch mutation of an unnamed plant of *Strobilanthes anisophyllus* that was growing in a field row at his nursery in Elsendorp, The Netherlands.

Asexual propagation of the new cultivar was first accomplished by the Inventor using softwood stem cuttings in August of 2008 in Elsendorp, The Netherlands. Asexual propagation of the new cultivar has determined that the characteristics are stable and are reproduced true to type in successive generations.

SUMMARY OF THE INVENTION

The following traits have been repeatedly observed and represent the characteristics of the new cultivar as grown in Elsendorp, The Netherlands. These attributes in combination distinguish 'Lankveld13' as a unique cultivar of *Strobilanthes*.

1. 'Lankveld13' exhibits leaves that are dark purple-black to dark green-purple in color.
2. 'Lankveld13' exhibits numerous lavender flowers per stem.
3. 'Lankveld13' exhibits a compact plant habit.

The parent plant of 'Lankveld13', an unnamed plant of *Strobilanthes anisophyllus*, differs from 'Lankveld13' in having lighter colored leaves, in having fewer flowers, and in having a plant habit that is less compact. 'Lankveld13' can also be most closely compared to the cultivar 'Brunetti' (not patented). 'Brunetti' is similar to 'Lankveld13' in having dark purple foliage, however 'Brunetti' differs from 'Lankveld13' in having white flowers and in having a less compact plant habit.

BRIEF DESCRIPTION OF THE DRAWING

The accompanying colored photographs illustrate the overall appearance and distinct characteristics of a 2 year-old plant of the new *Strobilanthes* as grown outdoors in a 3-liter container in Elsendorp, The Netherlands.

The photograph in FIG. 1 provides an overall view of the plant habit and blooming habit of 'Lankveld13'.

Figure 1:
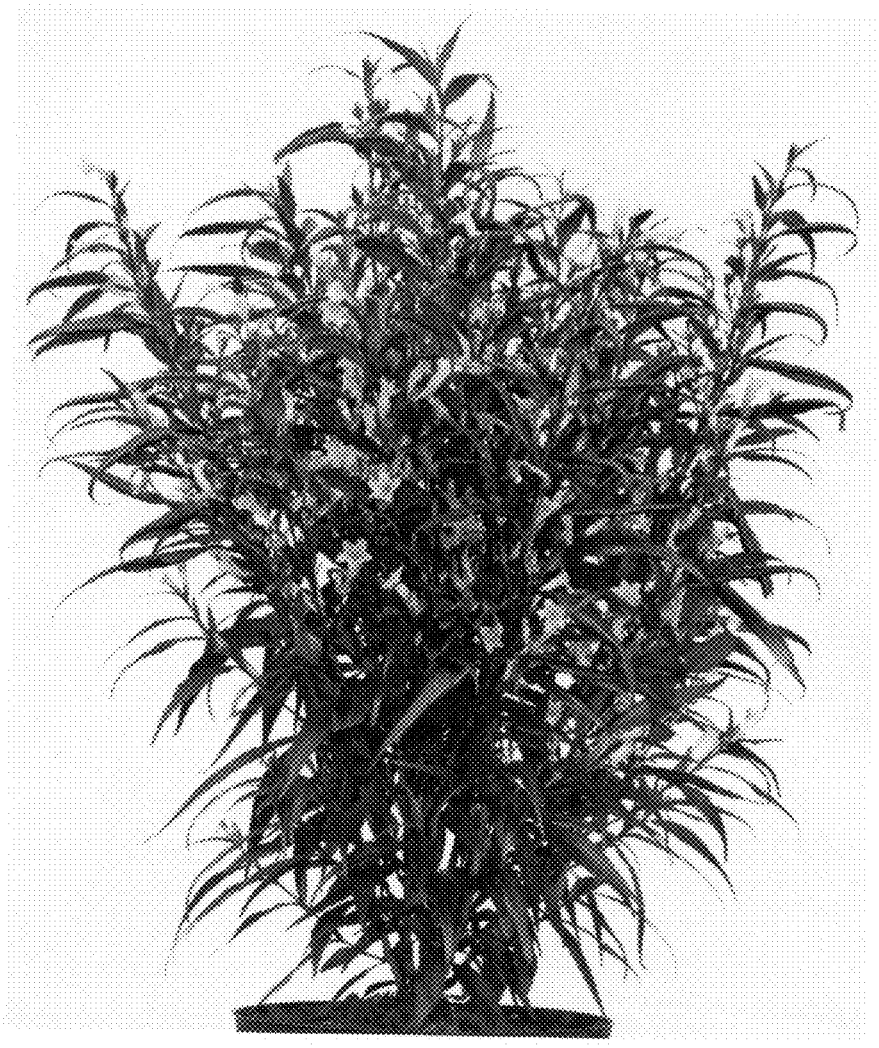
Figure 2:
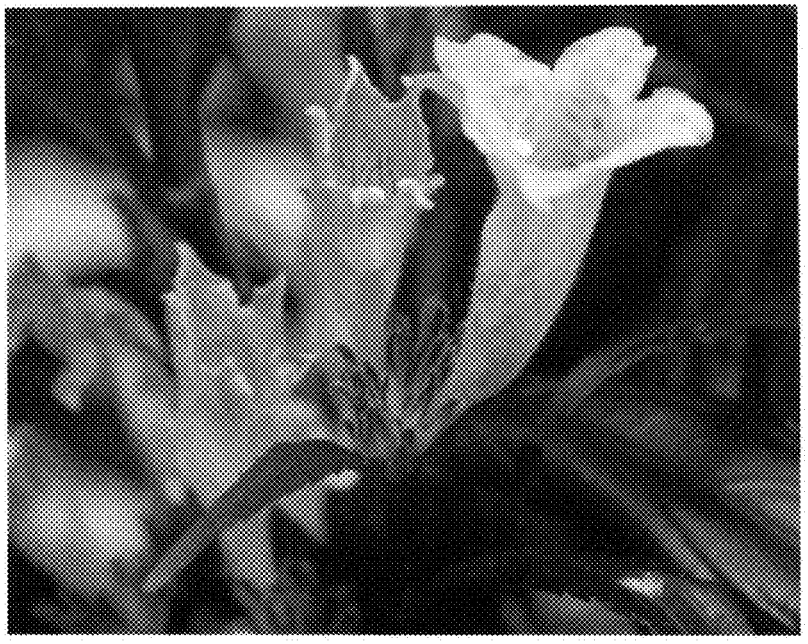

The photograph in FIG. 2 provides a close-up view of the flowers of 'Lankveld13'.

Figure 3:
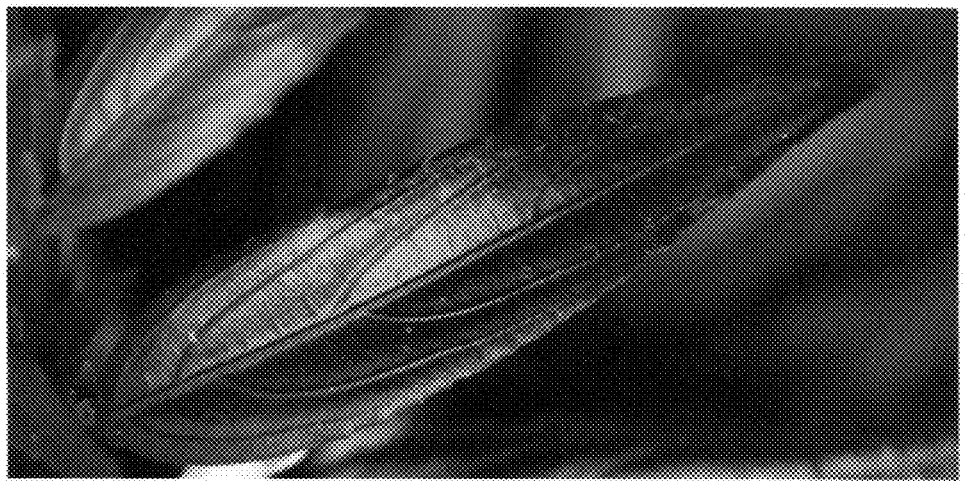

The photograph in FIG. 3 provides a close-up view of the foliage of 'Lankveld13'.

The colors in the photographs may differ slightly from the color values cited in the detailed botanical description, which accurately describe the colors of the new *Strobilanthes*.

DETAILED BOTANICAL DESCRIPTION

The following is a detailed description of 2 year-old plants of the new cultivar as grown in 3-liter containers in Elsendorp, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms spring to late summer in The Netherlands.

*Plant type*.—Evergreen shrub.

*Plant habit*.—Compact, narrowly upright.

*Plant size*.—Reaches about 50 cm in height and 44 cm in diameter.

*Hardiness*.—At least hardy to U.S.D.A. Zone 9.

*Diseases and pests*.—Not more susceptible to pests and diseases than other *Strobilanthes* varieties.

*Root description*.—Fibrous, moderately dense.

*Propagation*.—Softwood stem cuttings.

*Growth rate*.—Moderately vigorous.

Stem description:

*Shape*.—Quadrangular with slightly elevated angles.

*Stem color*.—146A, heavily tinged with colors ranging between N186C and 203A.

*Stem size*.—An average of 35.4 cm in length and 4 mm in diameter.

*Stem surface*.—Glabrous.

*Stem aspect*.—Average angle of 22.5° to the main stem.

*Stem strength*.—Very strong.

*Nodes*.—Thickened nodes, average of 5 mm in diameter, 146A in color and heavily tinged with colors ranging between N186C and 203A.

*Internode length*.—An average of 3.4 cm.

*Branching*.—Moderately free branching, an average of 15 lateral branches.

Foliage description:

*Leaf shape*.—Lanceolate.

*Leaf division*.—Simple.

*Leaf base*.—Attenuate.

*Leaf apex*.—Long apiculate.

*Leaf fragrance*.—None.

*Leaf venation*.—Pinnate, veins prominent, upper surface color 203B on purple-black leaves and a color between 139A and N189A on greener leaves, lower surface color between 187A on purple black leaves and 144A on greener leaves.

*Leaf margins*.—Shallowly serrate.

*Leaf arrangement*.—Opposite.

*Leaf attachment*.—Petiolate.

*Leaf surface*.—Both surfaces smooth, upper surface; glossy, lower surface; slightly glossy.

*Leaf size*.—An average of 8 cm in length and 1.7 cm in width.

*Leaf quantity*.—An average of 22 (11 pairs) per stem.

*Leaf color*.—Young upper surface; between N186A and 203A, young lower surface; a blend of 148A, 197A and 197B, tinged with N186C, mature upper surface; a blend of 203B, 139A and 189A, mature lower surface; between 139A and N189A.

*Petioles*.—About 6 mm in width and 1.5 mm in height, 147A and tinged with 187A, glabrous surface.

Inflorescence description:

*Inflorescence type*.—Axillary and terminal corymbs.

*Inflorescence size*.—Average of 25 cm in height and 1.6 cm in width.

*Flower buds*.—Narrowly oblong in shape, an average of 1 cm in depth and 0.4 cm in diameter, color 181C at apex, 200B in middle section and 144C at base.

*Flower fragrance*.—Produces a faintly spicy odor when rubbed specifically coming from the sepals.

*Lastingness of flowers*.—About 5 days.

*Flower aspect*.—Upright.

*Flower quantity*.—An average of 40 per stem, 4 per inflorescence.

*Flower shape*.—Unequal tubular-campanulate, typical for *Strobilanthes*.

*Flower type*.—Tubular.

*Flower size*.—Average of 1.6 cm in diameter and 25 cm in depth.

*Peduncles*.—Average of 2.3 cm in length and 1 mm in diameter, strong, average angle of 20° to the lateral branch, terminal peduncles in an average angle of 0° to lateral branch, between N186A and 203A in color, glabrous surface.

*Pedicels*.—None, sessile to peduncle.

*Calyx*.—Rotate in shape, an average of 8 mm in depth and 3.5 mm in width.

*Sepals*.—5, oblanceolate in shape, acute apex, fused base, lower 50% fused and free lobes have entire margin, an average of 8 mm in length and 1 mm in width, rotate and fused into a campanulate shape, both surfaces dull, outside of sepal densely covered with short glandular hairs, average length is 0.3 mm and NN155A in color, color: young upper surface; 200B, base 149B, young lower surface; 200B, base 144C, mature upper surface; 200B, base 149B, mature lower surface; 200B, base 144C.

*Petals*.—5, lower 85% fused into tube, narrow obovate in shape, margin entire on free portion, apex acute, an average of 2.6 cm in length with free portion an average of 0.5 cm in width, overall appearance of the petal is slightly glossy with tip curved to a 90° angle to the tube, inner surface is smooth, outer surface is densely covered with short soft hairs average length is 0.5 mm and 85C in color on the free lobes and 85D in color on the tube, inner surface is glabrous, color of inner surface when opening; 84B, tube 85D, veins 83D, base 163A to 163B, color of outer surface when opening; 84C, tube 85D, veins 84A, base 162A to 162B, color of inner surface when fully open; 85B to 85C, tube 85D, veins 83D, base 163A to 163B, color of outer surface when fully open; 85C, tube 85D, veins 84A, base 162A to 162B, petal color fading to 76B and then later becoming 165C.

Reproductive organs:

*Gynoecium*.—1 pistil, about 2.2 cm in length, style is an average of 2 cm in length, and NN155C to NN155D in color, stigma is pointed in shape and 155A in color, ovary is N172C in color.

*Androcoecium*.—4 stamens, diadelphous (2 short stamens, 2 longer stamens), short filaments are an average of 1.4 cm in length, long filaments are an average of 1.9 cm in length, NN155D in color, anthers are 155A in color, an average of 0.5 mm in length, and basifixed and ovate in shape, pollen is low in quantity and 158C to 158D in color.

*Fruit and seed*.—No fruit or seed production has been observed to date.

It is claimed:

1. A new and distinct cultivar of *Strobilanthes* plant named 'Lankveld13' as herein illustrated and described.

* * * * *